United States Patent [19]

Babb et al.

[11] 4,313,439

[45] Feb. 2, 1982

[54] AUTOMATED, SPRING-POWERED MEDICAMENT INFUSION SYSTEM

[75] Inventors: Albert L. Babb, Seattle; Richard E. Parks, Bellevue, both of Wash.

[73] Assignee: Biotek, Inc., Arlington Heights, Ill.

[21] Appl. No.: 133,320

[22] Filed: Mar. 24, 1980

[51] Int. Cl.³ .............................................. A61M 5/00
[52] U.S. Cl. ........................ 128/214 F; 128/DIG. 12
[58] Field of Search .......... 128/218 R, 218 A, 218 C, 128/213 R, 214 R, 214 F, 214 E, DIG. 1, DIG. 12, 234, 224

[56] References Cited

U.S. PATENT DOCUMENTS

| | | | |
|---|---|---|---|
| 3,472,226 | 10/1969 | Haber | 128/218 R |
| 3,884,228 | 5/1975 | Hahn | 128/214 F |
| 3,888,239 | 6/1975 | Rubinstein | 128/214 F |
| 3,985,133 | 10/1976 | Jenkins et al. | 128/214 F |
| 4,091,810 | 5/1978 | Lundquist | 128/214 F |
| 4,140,117 | 2/1979 | Buckles et al. | 128/213 R |
| 4,150,672 | 4/1979 | Whitney et al. | 128/214 F |

Primary Examiner—John D. Yasko

[57] ABSTRACT

A system is provided for the administration of a medicament, such as insulin, to a patient in small, controlled doses over an extended period in response to a continuously generated force. The force may be maintained continuously on a reservoir of the medicament in intermittent communication with a site in the body of the patient through a flexible and compressible tube. A constrictor about the tube keeps it normally closed except when a separate force is exerted to open the constrictor and permit the medicament to flow through the tube for a predetermined period. Alternatively, the continuously generated force may be applied intermittently to the medicament reservoir through the action of an escapement mechanism.

25 Claims, 5 Drawing Figures

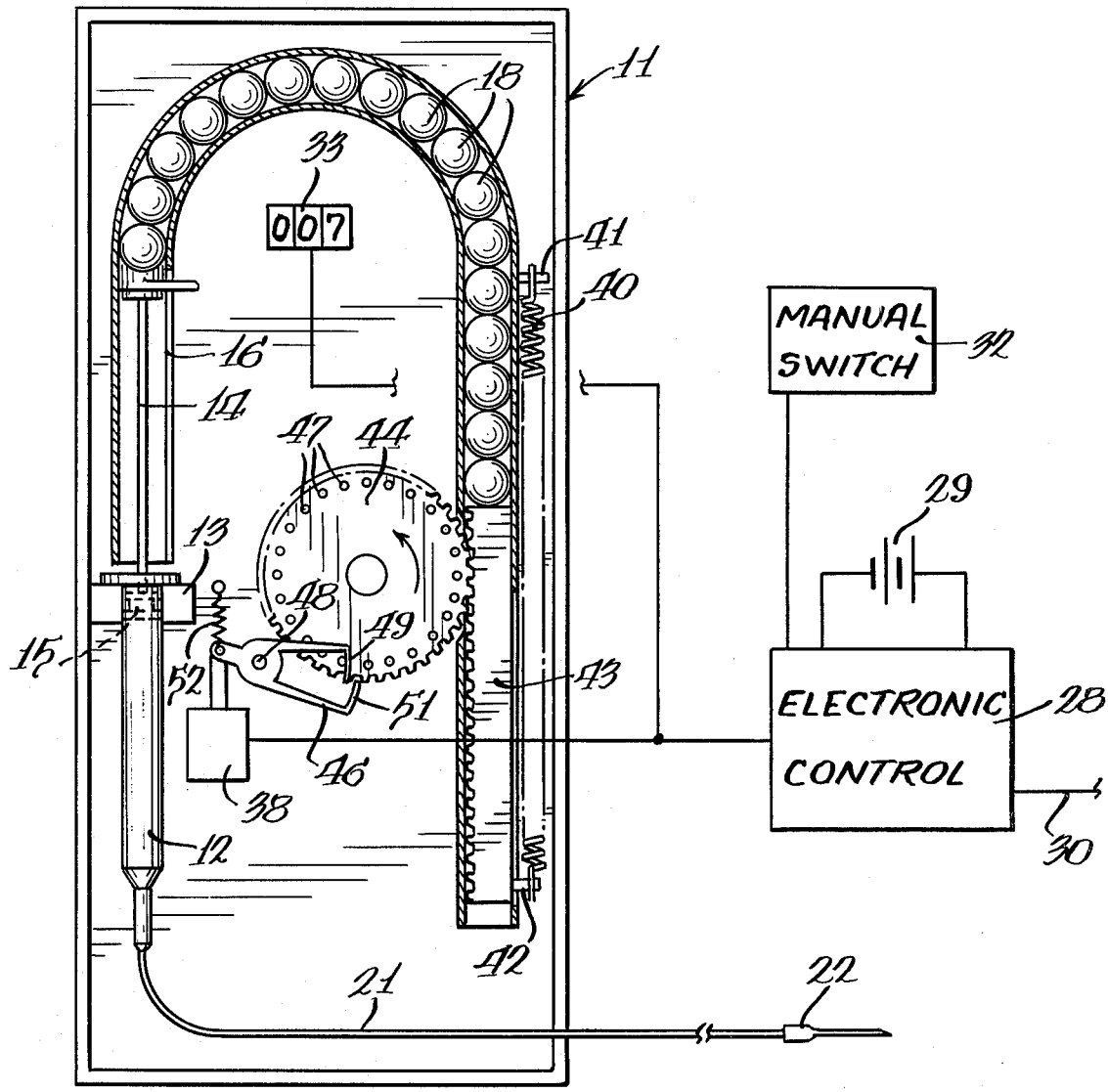

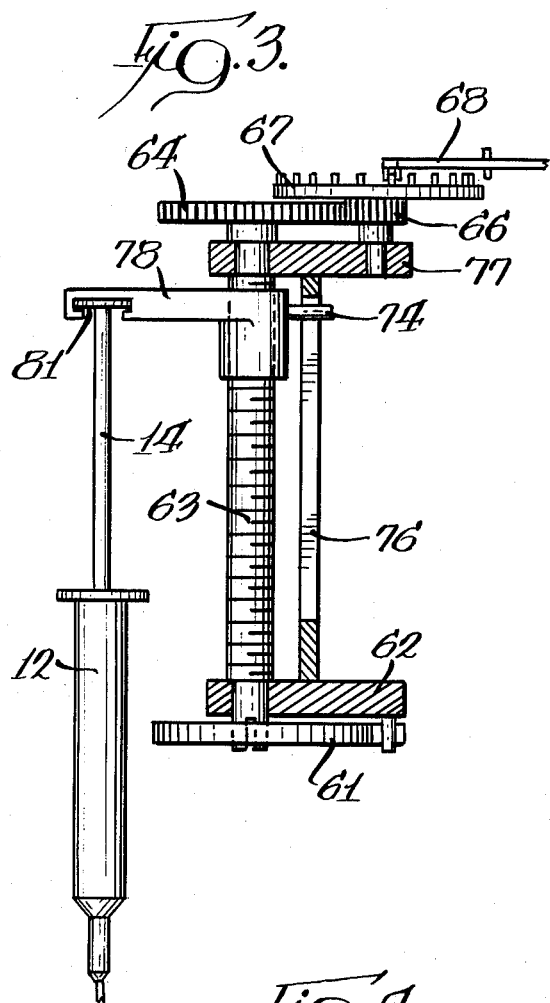
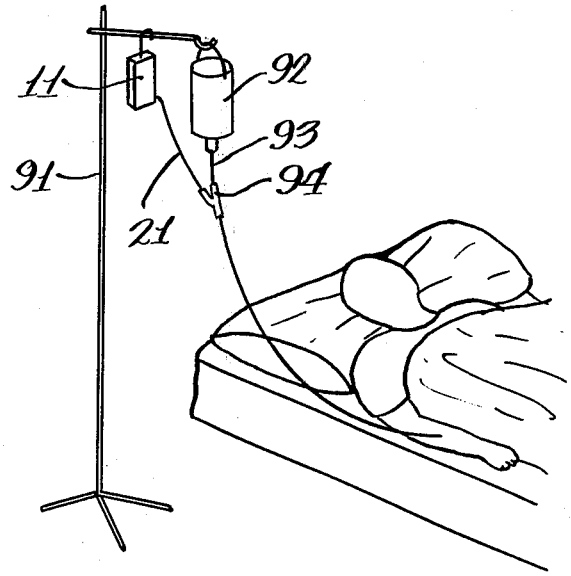
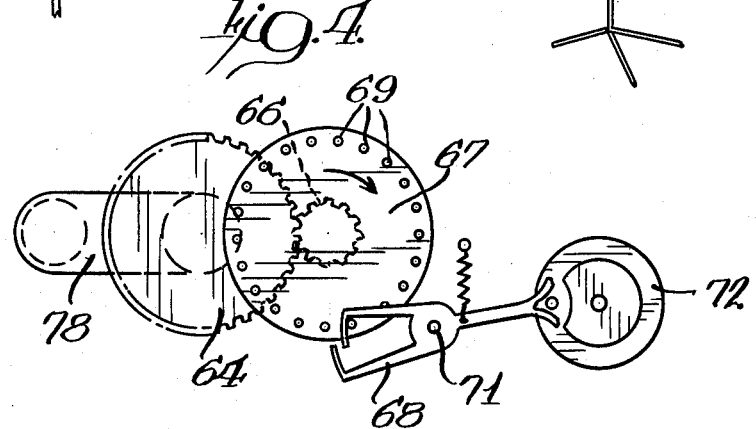

AUTOMATED, SPRING-POWERED MEDICAMENT INFUSION SYSTEM

TECHNICAL FIELD

This invention relates to a system for the administration of a medicament, such as insulin, to a patient in small, controlled doses over an extended period.

BACKGROUND OF THE INVENTION

There are many medical conditions which require the administration of liquid medicaments transcutaneously (through the skin) for prolonged periods. Diabetes, for example, may be controlled by daily, or more frequent, injections of insulin.

Since transcutaneous injections are painful and troublesome, and since each injection represents a possibility for infection, injections are spaced at intervals as far apart as possible, resulting in peak and valley concentrations of the medicament in the bloodstream or at the site in the body requiring the medicament, the peak concentrations occurring shortly after the administration of the medicament and the low, or valley, concentrations occurring shortly before the administration of the next injection. This method of administration exposes the patient to the possibility of overdose at peak levels and underdose at valley levels, but was nevertheless the standard method for many years in the absence of a better alternative.

Recently, systems have been developed in which a catheter is semi-permanently implanted in a patient to provide access to a transcutaneous site in a patient's body, and a liquid medicament is supplied to the catheter from a reservoir.

Insigler and Kirtz (Diabetics, 28: 196–203, 1979) describe a portable insulin dosage regulating apparatus which uses an electrically driven mini-pump with an insulin reservoir to periodically dispense a predetermined number of insulin units (U). A small electronic control box is used to set the basal rate of 0.4 U/hr in stages of 0.2 U each. A switch is used to trigger a program that infuses a higher dose for a period of one hour, after which the system automatically goes back to the basal rate.

Thomas et al. U.S. Pat. No. 3,963,380, issued June 15, 1976, describes a novel micropump driven by piezoelectric disk benders. Although the pump draws only a small current, it requires a voltage of about 100 volts to drive the pump.

Tamborlane et al. (The New England Journal of Medicine, 300: 573–578, No. 11, Mar. 15, 1979) describe a portable subcutaneous insulin delivery system which uses a battery driven syringe pump. The apparatus is bulky and heavy.

A peristaltic motor driven pump has been described by Albisser et al. (Med. Progr. Technol. 5: 187–193 [1978]). The pump weighs 525 g. and consumes 60 milliwatts at maximum pumping rates. This system has a continuous duty cycle. It is bulky and heavy and consumes a relatively large amount of power.

It is an objective of the present invention to provide a simple light weight system for the transcutaneous infusion of a liquid medicament into a patient in controlled doses over an extended period.

SUMMARY OF THE INVENTION

In accordance with one aspect of the present invention an apparatus is provided for the transcutaneous infusion of a liquid medicament into a patient in controlled doses over an extended period, comprising a syringe body, a plunger within the syringe body, means for generating force, means for applying the generated force to the plunger, means for regulating movement of the plunger in response to the applied force, and dispensing control means that provides a regulatory signal to the regulator means.

In particular, the syringe body includes an elongated barrel having an open end, a central passageway and a discharge end provided with a discharge aperture therein. A plunger is situated within the barrel and defines a medicament reservoir between the discharge end and the plunger. A delivery conduit means is provided communicating with the reservoir via the discharge aperture and, in turn, provides a medicament passageway for medicament delivery from the reservoir to a subcutaneous site in the patient. The force generating means, e.g., a kinetic energy source such as a spring, coacts with the means for applying the generated force to the plunger so as to effect movement of the plunger within the barrel. The medicament delivery regulator means is operably associated with the plunger and governs plunger movement in response to the applied force in response to a signal received from the dispensing control means that is operably associated with the regulator means.

In one aspect of the present invention the plunger movement is regulated by means of a hydraulic stop for the plunger, which stop is created by liquid medicament within the medicament reservoir upon pinching closed the delivery conduit.

In another aspect of the present invention the plunger movement is regulated by means of a mechanical stop that interrupts the movement of the means for applying the generated force to the plunger. The mechanical stop can be provided by an escapement mechanism which includes an escape wheel having a plurality of peripheral projections, such as teeth projecting outwardly from the circumference of the escape wheel or pins projecting upwardly from near the circumference. It also includes an anchor capable of oscillation and having two ends with a pallet at each end, the pallets being disposed in such a manner that each pallet alternately engages and releases each projection with each oscillation of the anchor and permits the escape wheel impelled by a continuously generated force to rotate intermittently by the circumferential distance between adjacent projections.

The oscillation of the anchor may be actuated by an electronic timing device, or the oscillation may be a harmonic oscillation imparted by a balance wheel.

In one embodiment of the apparatus of this invention, the conduit comprises a flexible and compressible tube, and there are also provided a means for transmitting a continuous force to said plunger, constrictor means about said flexible tube, said constrictor means having an open position which permits fluid passage through said conduit and a closed position which constricts said conduit transversely and cuts off fluid passage therethrough, closing means normally urging said constrictor means to its closed position, opening means to overcome said closing means and move said constrictor means to its open position, and means to actuate said opening means periodically for predetermined, usually short, time periods to permit small doses of said medicament to pass through said conduit to said subcutaneous site.

In accordance with another aspect of the present invention, a method is provided for the transcutaneous infusion of a liquid medicament into a patient in controlled doses over an extended period which comprises maintaining a reservoir of said liquid medicament in communication with a subcutaneous site in the body of said patient through a conduit, maintaining a constant impelling force, and intermittently forcing liquid medicament from said reservoir through said conduit to said subcutaneous site through the application of said impelling force on said liquid medicament in said reservoir.

In one embodiment of the method of this invention, a flexible and transversely compressible tube portion having a constrictable passageway therethrough is provided in the conduit, and the method includes maintaining a constant impelling force on said liquid medicament in said reservoir urging said liquid medicament through said conduit to said transcutaneous site, maintaining a transverse constricting force on said flexible tube to bar passage of said liquid medicament through said passageway, and periodically applying for predetermined time periods a force opposite to said transverse constricting force to overcome said transverse constricting force and thereby open said passageway to the passage of said liquid medicament under the influence of said impelling force.

More specifically, it is contemplated in this invention to utilize a standard insulin syringe, holding 100 insulin units in a 1 milliliter volume. In the above described embodiment, a uniform force is exerted on the plunger of the syringe by a small spring under compression.

In other embodiments of this invention, the impelling force is applied to the liquid medicament intermittently, that is, control of the flow of liquid impelled by the applied force is exerted above (or on the way to) the plunger through an escapement mechanism rather than downstream from the plunger on the flexible and compressible conduit.

BRIEF DESCRIPTION OF THE DRAWINGS

In the accompanying drawings forming part of the application:

FIG. 2 is generally similar to FIG. 1, but illustrating a second embodiment of the invention;

FIG. 3 is a fragmentary semi-schematic drawing illustrating an alternative mechanism for controlling and interrupting the transmission of a continuous force to the plunger of a syringe;

FIG. 4 is a top view of the mechanism of FIG. 3; and

FIG. 5 is a view in perspective of an embodiment in which the apparatus and method of this invention is utilized in conjunction with other transcutaneous treatment of the patient.

DETAILED DESCRIPTION OF THE INVENTION

Figure 1:
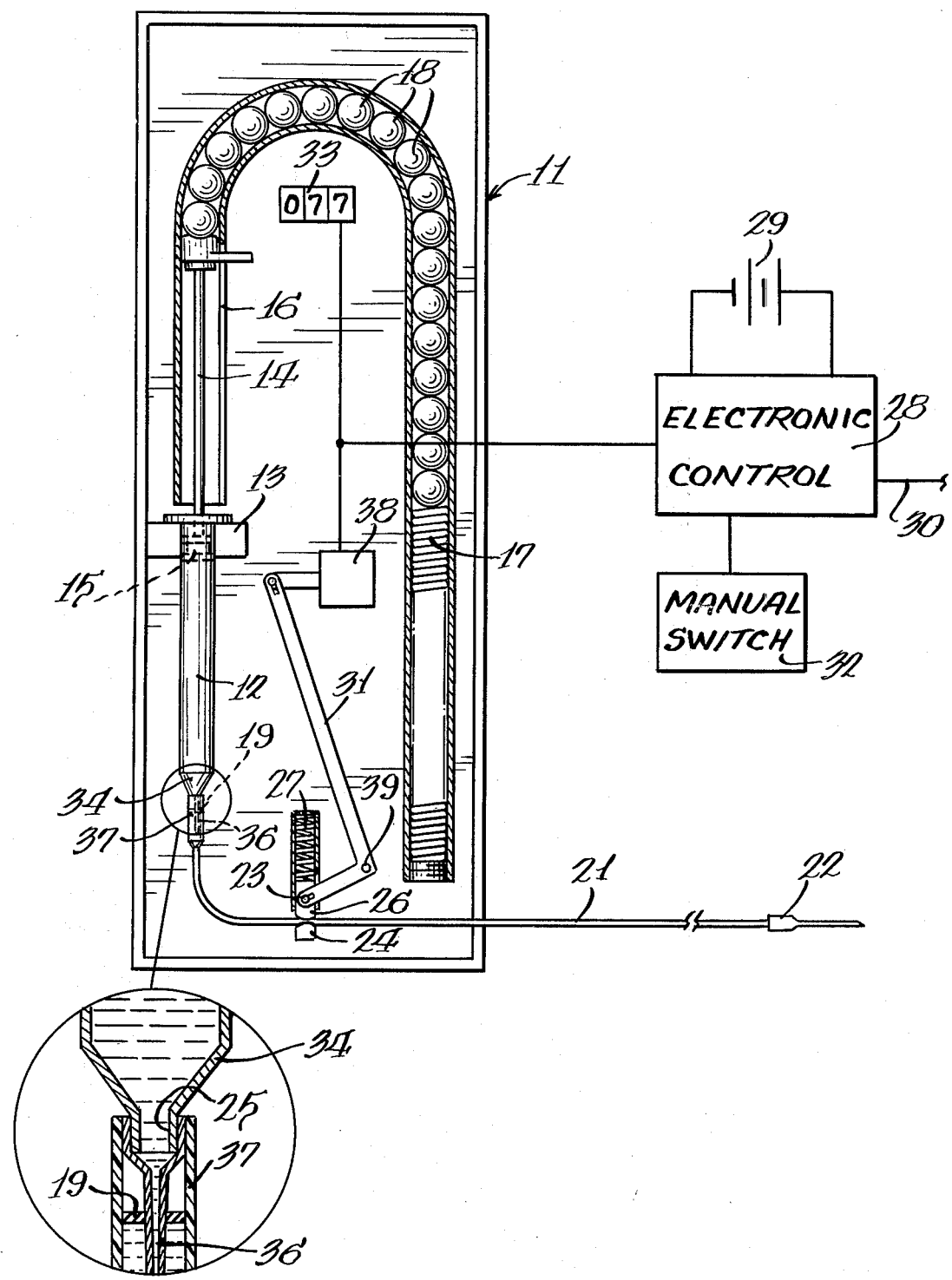
FIG. 1 is a semi-schematic drawing, partly in section, showing the relationship of the elements which make up the apparatus of one embodiment of the invention.

In the drawing of FIG. 1, housing 11 contains the coacting operating elements of the apparatus. A syringe, including syringe barrel 12 is held on the interior of housing 11 by clamp 13. Syringe plunger stem 14 is associated with plunger 15 and extends upwardly from syringe barrel 12 into guide tube 16, the amount of upward extension being dependent on the amount of liquid medicament in syringe barrel 12 below the plunger.

Guide tube 16 is shaped like an inverted "J" and spring 17, in compression, is at the end of guide tube 16 opposite the end into which syringe plunger stem 14 extends. A plurality of captured, aligned balls 18, positioned within guide tube 16, provide an operative connection to transfer force from compressed spring 17 to syringe plunger stem 14 and thus to plunger 15. The balls may be made of metal, plastic, or like non-compressible material.

At the discharge end 34 of syringe barrel 12, opposite the open end receiving syringe plunger stem 14 (as shown within the enlarged circle in FIG. 1), there is provided an aperture 25 which communicates with hypodermic needle 36, the latter penetrating self-sealing septum 19 within connector 37 at one end of tubes or conduit 21 at least a portion of which is flexible and transversely compressible. The opposite end of conduit 21 communicates with or is attached to hypodermic needle 22 for insertion through the skin of the patient, or for insertion into a pre-placed, implanted catheter providing access to a subcutaneous site within the patient's body. Needle 22 provides a constriction and thus increased hydraulic resistance in the system, the pressure upstream of needle 22 being substantially higher than the pressure downstream therefrom.

If desired, flexible and compressible tube 21 may be attached directly to syringe barrel 12 and in communication with aperture 25 by connector 37, eliminating hypodermic needle 36 and septum 19.

Constrictor 23 comprises stationary jaw 24 coacting with movable jaw 26 as well as compression spring 27 biasing movable jaw 26 toward stationary jaw 24 so as to compress flexible tube 21 to close its passageway. In the absence of any countervailing force, movable jaw 26 is generally close to stationary jaw 24 and the passageway in tube 21 is normally closed. In this manner the liquid medicament contained within barrel 12 provides a hydraulic stop which opposes movement of plunger 15 in response to the force generated by spring 17 when the flexible tube portion of conduit 22, held between jaws 24 and 26 is pinched closed.

Electronic control unit 28, energized by power source 29, e.g., a primary or secondary battery, is operatively attached to rocker arm 31 so that a periodic impulse from the time control unit operates solenoid 38 which moves rocker arm 31, pivotally mounted on pin 39, clockwise, and thus moves jaw 26 away from jaw 24 for a predetermined time interval, opening the passageway in tube 21 and permitting a measured amount of the medicament to pass through to needle 22 in response to the force applied to plunger 15. Thereafter jaw 26 is returned to its normally closed position close to jaw 24 by the action of spring 27 to interrupt medicament delivery.

Electronic control unit 28 may be a timer, a preprogrammed microprocessor receiving an input from an insulin demand sensor via lead 30, or the like. Control unit 28 may also include alarm systems that give a visual and/or audio indication when the amount of medication remaining in the reservoir is low or is exhausted, when the charge remaining in the power source is low, when there is an incomplete jaw closure, or when a similar condition of which the patient needs to be apprised arises.

Manual switch 32 is provided to override time control unit 28 and thus to permit the patient to administer an additional dose, or bolus, of the medicament to himself at will, whenever the patient requires more than the amount administered by the time control device. If desired, time control unit 28 can also be provided with means limiting the number of times manual switch 32 can be actuated within a predetermined time period. A guard (not shown) is provided over manual switch 32 to avoid accidental medicament administration.

Counter 33, connected to the solenoid 38, keeps count of the number of medicament emissions transmitted from the reservoir.

In a typical operation of the system of this invention for the administration of insulin to a diabetic patient, the time control device may be set to deliver one bolus of insulin every 360 seconds, or 360 boluses per 24 hour day. If the patient requires 50 U of insulin per day, each bolus contains 50/240, or 0.21 U of insulin. Since 100 units occupy one milliliter of the liquid, each bolus must contain 0.0021 ml, or 2.1 microliters of the liquid insulin.

Typically, a time period of 5 seconds of the 360 second cycle is used to drive the 2.1 microliters of insulin through the hydraulic resistance of needle 22 at a pressure drop ($\Delta P$) across the resistance (for a 28–30 gauge needle) of 150 mm Hg, or $2 \times 10^5$ dynes/cm$^2$ at the volumetric flow rate of $4.2 \times 10^{-4}$ ml/sec. The $\Delta P$ can be determined empirically or from the Hagen-Poiseuille equation:

$$\Delta P = 128 \, \mu V L / D^4$$

where $\mu$ is the liquid viscosity,
V is the volumetric flow rate
L and D are the length and diameter, respectively, of the resistance (i.e. needle 22).

The plunger has a $\frac{5}{8}$ inch diameter, or an area of 1.981 cm.$^2$. The force required on the plunger is therefore $2 \times 10^5$ dynes/cm $\times 1.981$ cm$^2$ = $3.96 \times 10^5$ dynes, or 0.899 lb$_f$.

In the embodiment of FIG. 2, elements similar to those of FIG. 1 are similarly numbered and perform the same function as discussed in connection with the embodiment illustrated in FIG. 1.

Referring to FIG. 2, spring 40 is a coil spring in tension, anchored at one end to support 41, affixed to housing 11, and attached at its opposite end to projection 42 on rack 43. The teeth of escape wheel 44 are engaged by rack 43 and wheel 44 is rotated counterclockwise, as shown by the arrow thereon, in response to urging by spring 40 via rack 43.

Escape wheel 44, however, is not free to rotate to the extent that it is impelled to do so by rack 43 and thus, in coaction with anchor 46, provides a mechanical stop for rack 43. The rotation of escape wheel 44 is made intermittent by the action of anchor 46 on pins 47 which project at right angles from the surface of the escape wheel 44, near its circumference. Anchor 46 is pivoted at mounting pin 48 to oscillate. Pallets 49 and 51, at opposite ends of anchor 46, alternately engage and disengage each successive pin 47 on the escape wheel as the anchor oscillates. Each oscillation of anchor 46 includes a counterclockwise rotation actuated by energized solenoid 38 in response to a signal from electronic time control 28 or as a result of the actuation of manual switch 32 followed by a return clockwise rotation actuated by spring 52 when solenoid 38 is de-energized.

In operation of the device of FIG. 2, rack 43 is continuously urged against incompressible balls 18 by the force of spring 40, and escape wheel 44 is therefore continuously urged to counterclockwise rotation. The rotation of escape wheel 44 is restricted, however, to intermittent progress through the action of anchor 46 with each rotational advance limited to a small arc corresponding to the distance between adjacent pins.

The intermittent rotation of escape wheel 44 permits an intermittent advance of rack 43 which movement is transmitted through balls 18 to plunger stem 14 and thus plunger 15, causing intermittent emissions of medicament from the reservoir of syringe barrel 12 through conduit 21 and hypodermic needle 22 to the patient.

Instead of rack 43 being driven by tension spring 40 as shown in FIG. 2, rack 43 can also be driven via escape wheel 44 when the latter is driven by means of a coil spring in a manner similar to coil spring drives utilized in conventional clock mechanisms. In such a case pins 48 also serve as mechanical stop means that interrupt the application of force to plunger 15.

In the embodiment of FIG. 3, a continuous driving force is provided by coiled main spring 61 anchored at one end to support 62 and arranged to supply a rotational force at its opposite end to screw 63 as in a conventional clock drive.

Screw 63 is journaled in supports 62 and 77. The upper end of screw 63 is axially affixed to relatively large gear 64 which meshes with relatively smaller gear 66, coaxial with escape wheel 67. The force of main spring 61, acting through the chain of drive elements comprising screw 63 and gears 64 and 66 tends to rotate escape wheel 67, but the rotation of the escape wheel is slowed down and made intermittent through the action of anchor 68 on pins 69 (see FIG. 4) of the escape wheel. Anchor 68 oscillates about pin 71, driven by balance wheel 72, which, in turn, is driven by a conventional hair spring (not shown). No electrical power source is required with this particular embodiment.

Rider 73 has an internal thread which engages the external thread of screw 63. Guide 74, integral with rider 73, fits loosely in a slot provided in support member 76, connecting support 62 to support 77. Extension arm 78, also integral with rider 73, is adapted to receive and hold disc 81 at the upper end of plunger stem 14.

In operation, coiled spring 61 applies torque on screw 63, and the rotation of screw 63 in response to the applied torque is controlled by escape wheel 67. Rider 73 moves slowly down the length of screw 63 as it rotates and plunger stem 14 is thereby moved slowly into syringe barrel 12 causing plunger 15 to expel medication contained within barrel 12.

In the embodiment of FIGS. 3 and 4 the incremental movements of plunger stem 14 are small and numerous so that the administered dosage, while actually incremental, is substantially continuous.

The devices of FIGS. 1, 2 and 3 are designed to be small, light and portable for use by ambulatory patients. However, they may, if desired, be used by bed confined patients to whom other liquids are being administered transcutaneously.

In FIG. 5, device 11 of this invention is suspended on rack 91 along with reservoir 92 which may contain an intravenous fluid such as a liquid nutrient or medicament. Tube 93, delivering the liquid from reservoir 92 to a vein in the arm of a patient is joined by conduit 21 from the device of this invention at Y-connection 94, preferably through a hypodermic needle and a self-sealing septum, as described in connection with FIG. 1.

The invention has been described with respect to the delivery of insulin to the patient. It is to be understood, however, that it is applicable to other medical treatments, such as the delivery of heparin to the bloodstream, delivery of chemotherapeutic agents to the bloodstream or to an organ, localized delivery of antibiotics to an infected area, or the localized delivery of analgesics to a painful area.

Other modifications and variations will be apparent to those skilled in the art.

We claim:

1. Apparatus for the transcutaneous infusion of a liquid medicament into a patient in controlled doses over an extended period, comprising a syringe including a plunger, and defining a cylindrical reservoir for said medicament and a discharge aperture; a conduit from said aperture to a subcutaneous site in said patient; means for generating a continuous force, and means for intermittently impelling said liquid medicament from said reservoir through said conduit to said subcutaneous site under the influence of said continuous force;

said means for intermittently impelling said liquid medicament through said conduit to said subcutaneous site including an escapement mechanism for transmitting said continuous force intermittently to said plunger; and said escapement mechanism including an escape wheel having a plurality of projections in the vicinity of its circumference and an anchor capable of oscillation about an axis and having two ends with a pallet at each end thereof, said pallets being disposed in such a manner that each pallet alternately engages and releases each projection with each oscillation of said anchor and permits said escape wheel to rotate intermittently by the circumferential distance between adjacent projections; and said apparatus including means to transmit said continuous force alternately to said escape wheel and to said plunger during each intermittent rotation of said escape wheel.

2. The apparatus of claim 1 including means to oscillate said anchor in response to an electronic control.

3. The apparatus of claim 2 wherein said electronic control is a timer.

4. The apparatus of claim 2 wherein said electronic control is connected to an insulin demand sensor.

5. The apparatus of claim 2 wherein said means for generating a continuous force comprises a spring in tension and said means to transmit said force to said plunger comprises a plurality of aligned balls within a tube.

6. The apparatus of claim 1 including means connected to said escape wheel to rotate a screw, a rider on said screw adapted to move axially thereon as said screw rotates, and means connecting said rider to said plunger.

7. The apparatus of claim 1 wherein said conduit includes a portion which is also a portion of a second conduit between said subcutaneous site and another liquid reservoir.

8. Apparatus for the transcutaneous infusion of a liquid medicament into a patient in controlled doses over an extended period, comprising a syringe including a plunger, and defining a cylindrical reservoir for said medicament and a discharge aperture; a conduit from said aperture to a subcutaneous site in said patient; means for generating a continuous force, and means for intermittently impelling said liquid medicament from said reservoir through said conduit to said subcutaneous site under the influence of said continuous force;

said conduit comprising a flexible and compressible tube and said apparatus also including means for transmitting said continuous force to said plunger; constrictor means about said flexible tube, said constrictor means having an open position which permits fluid passage through said conduit and a closed position which constricts said conduit transversely and cuts off fluid passage therethrough; closing means normally urging said constrictor means to its closed position; opening means to overcome said closing means and move said constrictor means to its open position; and means to actuate said opening means periodically to permit the doses of said medicament to pass through said conduit to said subcutaneous site.

9. The apparatus of claim 8 wherein said means for generating a continuous force comprises a spring in compression.

10. The apparatus of claim 8 wherein said means for transmitting said force comprises a plurality of balls in alignment within a tube.

11. The apparatus of claim 8 wherein said conduit includes a self-sealing septum at one end of said flexible tube and a hypodermic needle penetrating said septum and providing communication between said aperture and said conduit.

12. Apparatus for the transcutaneous infusion of a liquid medicament into a patient comprising a syringe body which includes an elongated barrel having an open end, a central passageway and a discharge end provided with a discharge aperture therein, a plunger situated within the barrel and defining a medicament reservoir between the discharge end and the plunger, delivery conduit means communicating with said reservoir via said discharge aperture and providing a medicament passageway for medicament delivery to a subcutaneous site in the patient, a force generating means, force application means operably associated with said force generating means for transmitting generated force to the plunger, medicament delivery regulator means operably associated with said plunger for governing plunger movement within the barrel in response to the applied force and including an escapement mechanism for interrupting application of generated force to said plunger, and dispensing control means operably associated with said regulator means.

13. The apparatus in accordance with claim 12 wherein said escapement mechanism is solenoid-actuated.

14. The apparatus in accordance with claim 12 wherein said escapement mechanism is balance wheel-actuated.

15. Method for the transcutaneous infusion of a liquid medicament into a patient in controlled doses over an extended period which comprises maintaining a reservoir of said liquid medicament in communication with a subcutaneous site in the body of said patient through a conduit which includes a flexible and transversely compressible tube having a constrictable passageway therethrough, maintaining a constant impelling force, and intermittently forcing liquid medicament from said reservoir through said conduit to said subcutaneous site in response to said impelling force on said liquid medicament in said reservoir by maintaining a transverse constricting force on said flexible tube to bar passage of said liquid medicament through said passageway and periodically applying a force opposite to said transverse constricting force to overcome said transverse constricting force and thereby open said passageway to the passage of said liquid medicament under the influence of said impelling force;

said constant impelling force being transmitted continuously to said liquid medicament in said reservoir.

16. The method of claim 15 wherein said periodic force is actuated by a timing device.

17. The method of claim 16 wherein said periodic force is additionally actuated by said patient at will.

18. The method of claim 15 wherein said periodic force is actuated by a predetermined medicament demand in the body of said patient.

19. The method of claim 15 wherein said reservoir is a syringe having a plunger and said impelling force is a spring in compression acting on said plunger.

20. The method of claim 19 wherein said impelling force is transmitted to said plunger through a plurality of balls aligned within a tube.

21. Method for the transcutaneous infusion of a liquid medicament into a patient in controlled doses over an extended period which comprises maintaining a reservoir of said liquid medicament in communication with a subcutaneous site in the body of said patient through a conduit, maintaining a constant impelling force, and transmitting said constant impelling force intermittently to said liquid medicament in said reservoir through an escapement mechanism which includes an oscillating anchor and an escape wheel driven to rotate by said constant impelling force by rotating said escape wheel through a predetermined arc at each oscillation of said anchor.

22. The method of claim 21 wherein said anchor is actuated to oscillate by a timing mechanism.

23. The method of claim 22 wherein said anchor is additionally actuated to oscillate by said patient at will.

24. The method of claim 21 wherein said anchor oscillates in harmonic rhythm imparted by a balance wheel.

25. The method of claim 24 wherein the rotation of said escape wheel causes the rotation of a screw and the rotation of said screw causes the movement of said plunger.

* * * * *